(12) United States Patent
Wilkins

(10) Patent No.: US 9,880,123 B2
(45) Date of Patent: Jan. 30, 2018

(54) CHIP FOR A PATHOGENS, PARASITES, TOXINS AND DESIRED CHEMICAL COMPOUNDS DETECTION

(71) Applicant: Ebtisam Wilkins, Albuquerque, NM (US)

(72) Inventor: Ebtisam Wilkins, Albuquerque, NM (US)

(*) Notice: Subject to any disclaimer, the term of this patent is extended or adjusted under 35 U.S.C. 154(b) by 816 days.

(21) Appl. No.: 13/986,636

(22) Filed: May 13, 2013

(65) Prior Publication Data

US 2014/0332409 A1    Nov. 13, 2014

(51) Int. Cl.
*G01N 27/327*    (2006.01)
*G01N 33/543*    (2006.01)

(52) U.S. Cl.
CPC ..... *G01N 27/3277* (2013.01); *G01N 27/3276* (2013.01); *G01N 33/5438* (2013.01); *G01N 33/54366* (2013.01)

(58) Field of Classification Search
CPC ............. G01N 27/327; G01N 27/3275; G01N 27/3276; G01N 33/5438; G01N 33/5302
See application file for complete search history.

(56) References Cited

U.S. PATENT DOCUMENTS

| | | |
|---|---|---|
| 4,813,424 A | 3/1989 | Wilkins |
| 4,986,271 A | 1/1991 | Wilkins |
| 5,431,160 A | 7/1995 | Wilkins |
| 5,476,776 A | 12/1995 | Wilkins |
| 6,180,335 B1 | 1/2001 | Wilkins |
| 7,931,788 B1 | 4/2011 | Wilkins |
| 8,652,311 B1 | 2/2014 | Wilkins |

OTHER PUBLICATIONS

Rao et al., "Comparison of different carbon ink based scree-printed electrodes towards amperometric immunosensing," World J. Microbiol. Biotechnol. (2006) 22:1135-1143.*
Yu et al., "A disposable amperometric immunosensor for α-1-fetoprotein based on enzyme-labeled antibody/chitosan-membrane-modified screen-printed carbon electrode," Analytical Biochemistry 331 (2004) 98-105.*

(Continued)

*Primary Examiner* — Alex Noguerola

(57) ABSTRACT

The present invention is directed to a method and apparatus for an immunoassay technique that uses amperometric measurements to rapidly analyze different pathogenic microorganisms, including bacteria, viruses, toxins, and parasites and chemical compounds using a disposable element. In accordance with one aspect of the present invention, at least one conductive immunosorbent is used to provide support for antibody immobilization and placed on the top of the working electrode; it could also be used by itself as a working electrode. This immunosorbent or powder can be fabricated of conductive material or nonconductive material over which a conductive material is coated. A membrane cover of the working electrode forms a fluidic chamber having a pore size that is suited to the particular application to insure no contact between the working electrode and counter or silver electrode. The immunoassay can be automated using microprocessor control to reduce the amount of human intervention.

14 Claims, 3 Drawing Sheets

(56) References Cited

OTHER PUBLICATIONS

Tu et al., "The fabrication and optimization of the disposable amperometric biosensor," Sensors and Actuators B: Chemical vol. 80, issue 2, Nov. 20, 2001, pp. 101-105.*

Wikins E. and Sitdikov R., "Biosensors for Viruses Detection". Chapter 21 in Smart Biosensor Technology. Editor George K Knopf. CRC Press, p. 567, 2007.

1 Abdel-Hamid I., lvnitski D., Wilkins E., "Highly sensitive flow-injection immunoassay system for rapid detection of bacteria", Anal.Chim. Acta ,399, 99-108, 1999.

Shah J., Chemburu S.,., Wilkins E., Abdel-Hamid I, "Detection of E.Coli using Graphite Coated Nylon Membranes," Electroanalysis, vol. 15, 1-6, 2003.

Ivnitski D., Abdel-Hamid I., Atanasov P., and Wilkins E., "Biosensors for Detection of Pathogenic Bacteria (A Review)". Biosensors and Bioelectronics, 14, 599-624, 1999.

Hurst M., Wilkins E., "Chemical and Biological Warfare: Should Rapid Detection Techniques Be Researched to Dissuade Usage?", International Journal of Applied Sciences, 2 (4) 796-2005.

Vetcha S., Abdel-Hamid I., Atanasov P., Ivnitski D., Wilkins E.,"Portable Immunosensor for the Fast Amperometric Detection of Anti-hantavirus Antibodies", Electroanalysis, 12, (#13), 1034-1038, 2000.

Wikins E. and Sitdikov R., "Biosensors for Viruses Detection". Chapter 21 in Smart Biosensor Technology. Editor George K Knopf. CRC Press, p. 567, 2007. Invited.

Sitdikov R., Ivnitski, D., Abdel-hamid, I., and Wikins E., "Detection and Identification of Organophosphorous compounds: As Chemical warfare agents". CRC publications, 293-313 CRC publications, Tylor & Francis group, 293-314, 2010. Invited.

Carnes E., Wilkins E., "The development of a new, rapid, amperometric immunosensor for the detection of low concentrations of bacteria. Part I: Design of the detection system and applications". American Journal of Applied Sciences., vol. 2, No. 3, 597-606, 2005.

Sitdikov R and Wikins E. "Detection of Para Influenza and Influenza A Viruses Using Flow-Injection Amperometric Immunosensor", Journal of Applied Research, vol. 7, No. 1, 108-126, 2007.

Sitdikov R, Wikins E, Yates T, Hjelle B.,"Detection of Hantavirus Using a New Miniaturized Biosensor Device" Journal of Applied Research, vol. 7, No. 1, 86-107, 2007.

Wikins E. and Sitdikov R., "Biosensors for Hanta, Influenza A, and Para Influenza Viruses Detection". Chapter 22 in Smart Biosensor Technology. CRC Press, p. 597, 2007.

Carnes E., Wilkins E., "The development of a new, rapid, amperometric immunosensor for the detection of low concentrations of bacteria. Part II: Optimization of the system for *Escherichia coli*". American Journal of Applied Sciences. vol. 2, No. 3., 607-613, 2005.

Ghindilis,A.L. , Atanasov P., Wilkins M., and Wilkins E., "Immunosensors: Electrochemical Sensing and Other Engineering Approaches (A Review) ". Biosensors and Bioelectronics, 13, 113-131, 1998.

Ghindilis A.L., Krishnan R., Atanasov P. and Wilkins E., "Flow-through Amperometric Immunosensor: Fast "Sandwich Scheme" Immunoassay", Biosensors and Bioelectronics, 12 (1997) 415-423.

Abdel-Hamid I., Ivnitski D., Wilkins E., "Highly sensitive flow-injection immunoassay system for rapid detection of bacteria", Anal.Chim. Acta ,399, 99-108, 1999.

Vetcha S., Yates T., Wilkins E., "Detection of Hantavirus Infection in Hemolyzed Mice Blood Using Alkaline Phosphatase Conjugate ", Biosensor and Bioelectronics, #17, 910-909, 2002.

Chemburu S., Wilkins E., "Detection of Pathogenic Bacteria using Highly Dispersed Immunoelectrodes", Biosensors & Bioelectronics, 21,491-499,2005.

Shah J., Wilkins E., "Biosensors for Detection of Biological Warfare Agents", Electroanalysis, vol. 15, No. 3, 157-167, 2003.

Ivnitski D., Atanasov P., Abdel-Hamid I., Wilkins E., (Review), "Application of electrochemical biosensor for detection of food pathogenic bacteria", Electroanalysis, 12, 317-325,2000.

Vetcha S., Wilkins E., Yates T., "Detection of Hantavirus Infection in Hemolyzed Mice Blood Using Alkaline Phosphatase Conjugate ", Biosensor and Bioelectronics, #17,(10), 910-909,2002.

Vetcha S., Yates T., Hjelle B., Wilkins E., "Rapid and Sensitive Handheld Biosensor for Detection of Hantavirus Antibodies in Wild Mouse Blood Samples Under Field Conditions", Talanta, #58, 517-528, 2002.

* cited by examiner

CHIP FOR A PATHOGENS, PARASITES, TOXINS AND DESIRED CHEMICAL COMPOUNDS DETECTION

RELATED APPLICATIONS

The present application is a continuation-in-part of parent application Ser. No. 13/065,926, filed Apr. 1, 2001, now U.S. Pat. No. 8,652,311, which is a continuation-in-part of application Ser. No. 11/537,915, filed Oct. 2, 2006, now U.S. Pat. No. 7,931,788.

BACKGROUND OF THE INVENTION

Pathogens, such as bacteria, parasites, toxins, and viruses, have emerged as public health problems. Worldwide, pathogenic infections are responsible for more deaths than any other cause. At times, the pathogens are opportunistic when our resistance is low due to Acquired Immuno Deficiency Syndrome (AIDS), immunosuppressive drug therapy, anticancer treatment, or other related factors. Food borne disease outbreaks, emergence of newer strains of drug-resistant bacterial pathogens without any forewarning (such as the recent outbreak of Severe Acute Respiratory Syndrome [SARS] in Asia), Bird Flu, or pathogens used as a potentially viable source of biological warfare weapons for mass destruction, necessitate the development of a rapid, portable, analytical device as an early warning system for real-time detection of bacterial pathogens in field conditions.

U.S. Pat. No. 7,931,788 discloses a flow over assembly for the detection of bacterial contamination in the food processing industry. The circuit content of U.S. Pat. No. 7,931,788 and U.S. Pat. No. 8,652,311 is incorporated by reference to it herein. The disposable element disclosed in the patent includes an immunosorbent layer having antibodies or antigen to a target microbe affixed thereto, a membrane or carbon powder in support of the immunosorbent layer, and three electrodes for detecting electrochemical signals. The disposable element may be used to measure the level of microbiological contamination in a solid sample caused by a predetermined microbe. This disposable sensor element cannot be used as a commercial product. However, the U.S. Pat. No. 7,931,788 patent is directed to the detection of food contaminations. The disposable element in U.S. Pat. No. 7,931,788 contains a pre-filter, three ports, and at least one electrode, all of which increase the size of the disposable element and add unnecessary costs to the assay. Further, in the patent, the filtration membrane used in support of the immunosorbent layer is not conductive, necessitating the presence of an electrode in close proximity to the membrane in order to accurately measure the changes in electron transfer. This application therein is a chip used to make a biosensor.

A new, simple, disposable element carbon strip chip is developed, designed, and tested. For commercialization, a need exists for a disposable sensor with Antigen or Antibodies to be immobilized so any analytes could be readily tested. Eliminating the bulky sensor was in the U.S. Pat. No. 6,180,335, and the U.S. Pat. No. 7,931,788. Therefore, a disposable element needs to be developed, designed, and tested. For commercialization with Antigen or Antibodies immobilized on the immunosorbent so any analytes could be readily tested. This is the subject of this patent application.

SUMMARY OF THE INVENTION

This application describes a rapid, portable, analytical device which can be used as an early warning system for real-time detection of bacterial pathogens in field conditions.

Advantages of the technology described herein include decreased analysis time, increased sensitivity, simplification, and automation of the measuring procedure, which produces quantitative results, decreased cost, and portability, all of which allows use under non-laboratory and field conditions. The technologies provide results in about 20 minutes; a requirement of only five to ten percent of the time of most current test procedures. A single-channel functional prototype device has been thoroughly tested and used in the experimentation with various analytes. Conceptual designs have been completed for other configurations (including a multi-channel, multi-analyte device) to address a variety of applications. The portability and speed revealed in the tests will provide substantial advantages over current practices in these markets. The seriousness of food poisoning alone is exemplified by frequent exposure in the popular press.

The standardized, automated carbon screen print electrode diagnostic process, when combined with the system's reduced size, will permit trained technicians (rather than scientific specialists) to use it onsite as well as in a laboratory setting. The technology has been developed for a number of analytes including IgG, IgM, *E. Coli* O157R7, total *E. Coli*, *Staphylococcus* sp and Hanta-virus. Tests for *Salmonella* and Hepatitis are in process.

The technology provides a general methodology for fast, sensitive, inexpensive and portable immunoassays over a wide range of analytes such as bacteria, fungus, viruses and chemicals. Since this technology offers a faster and cheaper method of employing test procedures that are already approved, regulatory issues are dramatically reduced. Additionally, current conventional immunoassay techniques are comparatively lengthy analyses that usually take several hours.

The carbon screen print electrode improves upon conventional immunoassay techniques by the enhancement of immunointeraction efficiency; this is accomplished by using a flow over assay technique, which employs a microfluidics chamber over the working electrode filled with immunosorbent. This provides a high area-to-volume ratio of solid-to-liquid phase and leads to a high rate of immunointeraction due to reduced diffusion limitations. Another area of improvement is the development of a faster and more sensitive detection method using electrochemical detection of the labeled immunospecies.

The potential applications of this novel immunoassay are based upon its advantages relative to existing techniques, namely:

1) It is 20 to 30 times faster
2) It is a highly-automated assay that can be conducted by less-trained personnel
3) It can be configured as a portable device, which allows assays to be conducted in the field.

The technology is based on a "sandwich" scheme, which is more sensitive than the usual "displacement" scheme. It is especially effective for large molecular-weight analytes, which represent the vast majority of applications in the target industries.

The present invention is directed to an immunoassay and a disposable sensing element that uses amperometric measurements to rapidly detect and analyze different pathogenic microorganisms, including bacteria and viruses, toxins, fungi, and parasites. In accordance with one aspect of the present invention, the immunosorbent powder is used to provide a surface for antibody or antigen immobilization and placed on the top of a working electrode. This immunosorbent can be fabricated using conductive powder, such as all types of carbon powder or conductive polymer.

The proposed technique is adaptable for use with different materials such as carbon powder, graphite, ULTI carbon (Ultra Low Temperature Isotropic carbon), conductive polymers, or any other conductive powder so as to form the immunosorbent. Another aspect of the present invention relates to a compact and simple disposable element that can be easily assembled and disassembled or completely disposed of. In still another aspect of the present invention, the immunoassay is now automated; using microprocessor control so as to reduce the amount of human intervention in sample analysis.

In summary, this broad-based technology was developed using a "sandwich-scheme" immunoassay with enzymatic labeling and amperometric signals. It has been incorporated in an automated, portable device, and connected to a carbon screen print electrode. It is a functional prototype which provides for highly-sensitive, quantitative detection of levels of most large molecules in a sample. In addition to detecting pathogenic infections, applications are numerous in such fields as medical and veterinary diagnostics, food processing quality control, epidemiology field analysis, and environmental chemical analyses. Anticipated products include a variety of automated devices with substantial competitive advantages and a series of disposable flow over carbon screen print electrodes specific to each analyte to be diagnosed. Proprietary cartridges of commercially available immunochemicals will be part of the automated process.

DETAILED DESCRIPTION OF THE INVENTION

One aspect of the present invention relates to the use of conductive powder, which acts as a support for antibody immobilization and is placed on the top of the working electrode. Since the immuno-interactions and amperometric measurement occur at the same sites, a significant increase in the magnitude of the electrochemical response is resulted due to high surface-to-volume ratio of the powder.

In one embodiment, the carbon, graphite, carbon black, or ULTI powder can be further processed for immobilizing the desired antigen or antibody by well-established method in the art, such as the use of Woodward's reagent K. The present invention should not be limited to the one embodiment wherein other types of porous powder materials may also be used if the conductive material that is capable of accepting immobilization of an Antibody or Antigen, including, but not limited to, graphite/carbon, or conductive polymers.

Another aspect of the present invention relates to a compact, yet low-cost, disposable unit for flow over immunoassay measurements.

The focus on development of a disposable sensing element for an automated simple single or more channels on-line flow over immunoassay amplification procedure and amperometric biosensor that we have already developed for fast, quantitative detection of low concentrations of total *E. coli*, *S. Aureus*, hantavirus, influenzas, and other pathogens have been tested. Qualitative detection of low concentrations of Hantavirus, influenza A, bird flu, and Para influenza has been tested. The system will be arranged as a portable device and results will be confirmed using carbon screen print electrodes. All components are easily accessible allowing ease of service and maintenance. Further utilization of amperometric detection in comparison to spectrophotometric detection allows for the substantial limitation of reagent consumption, eliminating optical elements from the measuring device. The use of higher working dilutions of blood sample (1:200-1:500) minimizes the interference effects and allows one to ignore the difference in the color and turbidity of natural samples for Hantavirus. This device was found to be robust in field operations: in terms of accuracy, reproducibility, and ease of use, sensitivity and ability to compensate for interference. The device exhibits good response stability. The sensitivity of the carbon screen print electrode is great. In the preliminary evaluation we anticipate no false positive or false negative samples with 100% accuracy using Hantavirus rodent blood.

Engineering of the Disposable Sensing Element

The design includes disposable sensing elements, development, and standardization of an immuno biosensor.

Figure 1:
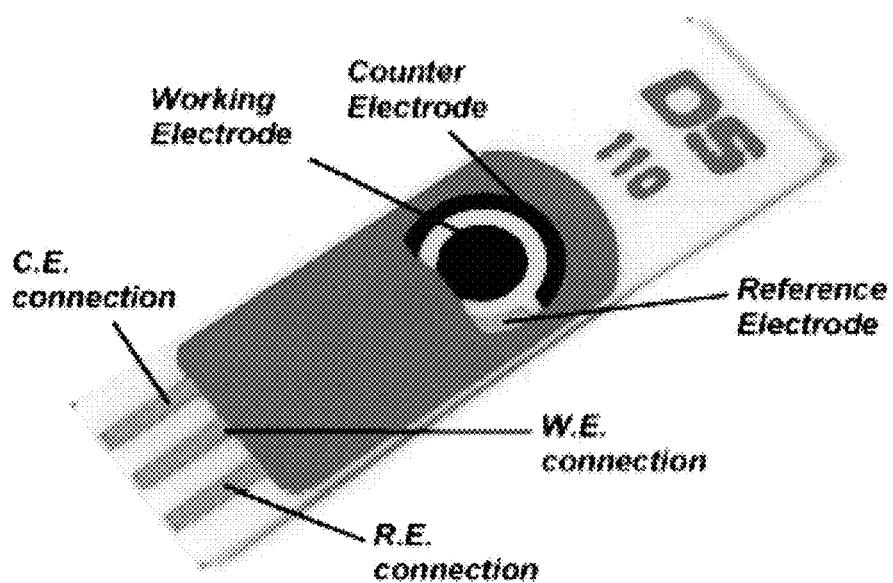
FIG. 1 is a carbon screen sensor; a chip with three electrode system. A working and counter electrodes made of carbon, a reference electrode made of silver.
Figure 2:
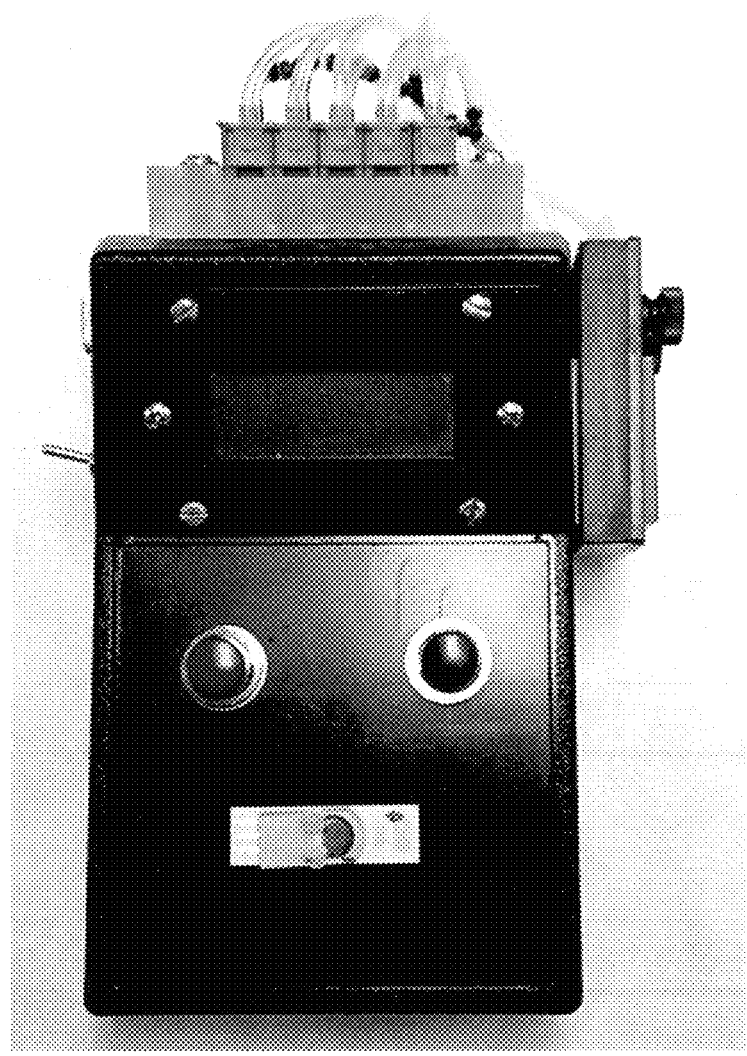
FIG. 2 is a biosensor carbon screen system. The assembly, when connected to the test device of the U.S. Pat. No. 7,931,788 and U.S. Pat. No. 8,652,311, incorporated by reference to it herein, or any other wireless technology with conductive lead can be used to transfer and record the signal. The fluidic chamber is shown with connecting tubes to the inlet and outlet showing carbon in it.

The disposable sensing elements illustrated in FIG. 1 has been engineered in the form of one or more parallel channel cartridge(s) as for simultaneous measurement of total *E. coli*, *S Aureus*, Hantavirus, and bird flu in bio-samples, as well as other pathogens and compounds without pre-enrichment. The biosensor chip has to be built with microfluidics chamber as described in FIG. 1.

The setup with a printed screen disposable element could function with an electric circuit like that which was described in the U.S. Pat. No. 7,931,788, or any other wireless technology can be used to transfer and record the signal. The device should exhibit good response stability when tested. The sensitivity of the carbon screen print electrode was 100% in this preliminary evaluation; with anticipation of no false positive or false negative samples using Hantavirus rodent blood and other pathogens.

Testing of different IgG (Immunoglobulin) concentrations confirmed the results with ELISA (enzyme-linked immunosorbent assay) data. Initial studies have used laboratory cultures of *coli* form bacteria at known low and high cell concentrations. The total number of bacteria in each sample has been known.

The main characteristics of the portable carbon screen print electrode biosensor are flow rate, incubation time, concentrations of conjugate and substrates, volume of sample, working temperature, configuration, and geometric parameters of the flow over the electrochemical sensor.

A multi-channel carbon screen print electrode sensor element inlet and outlet for the flow of analytes connected to the electronic circuit with electronic valves described in U.S. Pat. No. 7,931,788 (or any other wireless technology) can be used to transfer and record the signal. The effect of such factors as the pore size and membrane type, flow rates and temperature on the transport phenomena has been also investigated. An assembly to be used in a flow over immunosorbent, comprising: a layer of immunosorbent having immobilized antibodies that bind to a target analyte in a sample solution; a screen printed electrode comprising of at least one working electrode, when the immunosorbent (paste) is inserted into the disposable unit, forms electrical contact with said working electrode, and with electrochemical communication with the other electrode system; with inlets which are capable of passing the flow solutions during the immunoassay; and an outlet which goes to disposal.

Fabrication of One or More Electrochemical Biosensor Prototype(s)

The previous version of the chip design needed to be modified by using a different membrane over the working electrode to incorporate any loose carbon powder. Due to the development of new, automated embodiments, one or more channels of electrochemical biosensor prototype can be added. This has been used to develop a one-channel, automated electrochemical biosensor for commercial use. Additional channels can be added to the system consisting of more channels amperometric disposable sensing elements in a rotating cartridge. This was not working well without the fluidic chamber.

Preferably, a disposable multi-unit (disposable element), as illustrated in FIG. 11 of U.S. Pat. No. 8,652,311 B1, could have other shapes that may also be used. The previous version of the biosensor chip design using one channel has to be modified by using a hydrophilic vertical pore membrane AR Care® 92205 cover over the working electrode in order to incorporate any loose carbon powder and prevent contact with the other two electrodes. Initially using a covering membrane on the top of the working electrode with a larger pore size than the powder that resulted in leaking of some of the carbon powder. Therefore, a membrane with a smaller pore size has to be used to prevent powder particles from leaking and to prevent the presence of loose carbon. This can be accomplished by adding an extra layer of membrane to the design with a smaller pore size. A membrane with a larger pore size was used and it was found that the membrane could not retain most of the carbon. Some loose powder was flushed during the test.

One embodiment of the present invention had a membrane which adhered to the chip on the top of the working electrode to ensure no contact between the working electrode and immuno sorbent. Another membrane was put on the top of the counter and the reference electrodes to ensure communication between the three electrodes. Also it should prevent the leak of the modified carbon. The modified carbon or graphite powder was then applied on the top of working electrode. The modified carbon is inserted over the working electrode only, then insert a micro fluidics chamber, which was assembled to the chip. Now the chip system is completely assembled and operational.

In another embodiment, the porous membrane is to be put on the top of the working electrode to spatially retain the modified carbon immunosorbent and prevent electrical shorting of the electrodes or signal generation at the reference and counter electrodes. The membrane is capable of being a cover for the immobilized immuno-sorbent to retain the carbon particles and keep it from leaking through the outlet opening of the sensor or the membrane pores.

In yet another embodiment, conductive material such as highly dispersed fine carbon particles, called Ultra Low Temperature Isotropic carbon (ULTI) is used.

A preferred embodiment: The entire assembling process in the old previous sensor flow over has to be eliminated and now the chip is simpler and easy to operate. Therefore the disassembling process after the completion of an experiment is simply discarding the used carbon screen print electrode. For every new immunoassay, a new disposable unit is used, ensuring both accuracy and efficiency. Further, an array of the disposable sensor unit can be prepared, having different antibodies or antigens immobilized on the surface of the immunosorbent for the detection of a wide range of pathogens, including, but not limited to, bacteria, viruses, parasites, DNA, or toxins.

The present invention further relates to an automated system of flow-through immunoassay. In a preferred embodiment a system, such as described in U.S. Pat. No. 7,931,788 or any other wireless technology can be used to transfer and record the signal.

There are many advantages of using the automated immunoassay carbon screen print electrode system as disclosed in this current invention. The assay is completely automated so that little human intervention is needed to complete an assay. Further, the assay can be stopped or started at any stage of the process. The total assay time is reduced when compared with the time required for manual assaying and the data acquisition can be connected via a wireless phone or to a computer or data storage unit for analysis or storing. Additionally, different assay procedures can be programmed so that the system can be easily adapted for the detection of different pathogens.

Example 1

Controlled Experiment Using Cyclic Voltammetry with Ferricyanide.

Figure 3:
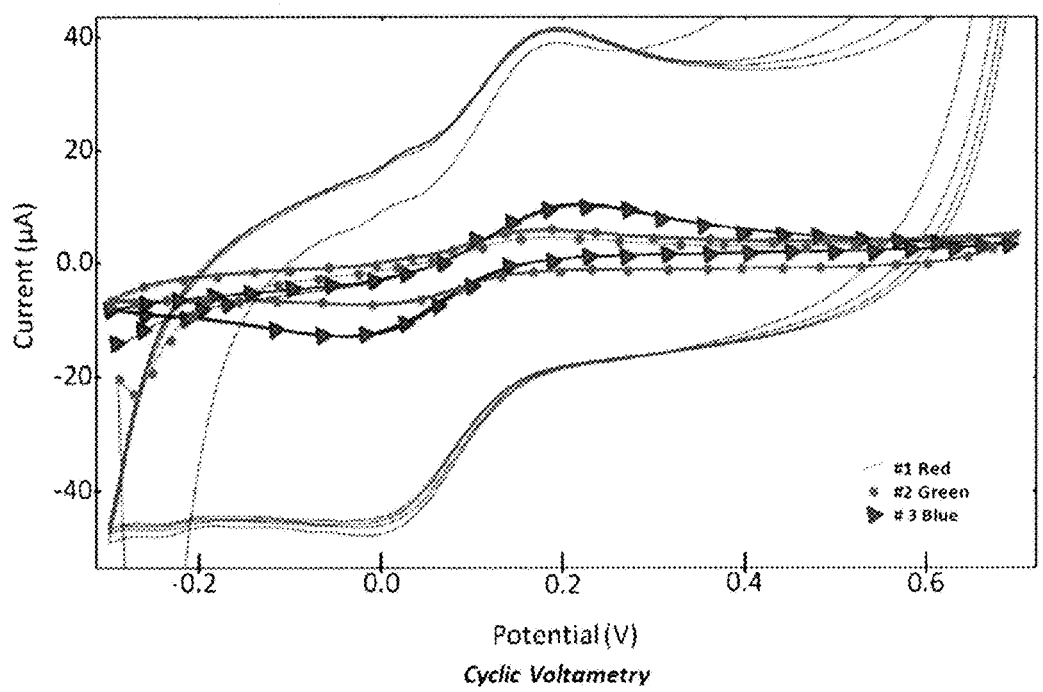
FIG. 3 is the micrograph from Cyclic Voltammetry (CV) of ferrocyanide testing, which was performed using the assembled disposable sensing element. Red represents: Activated Screen Printed Carbon+membrane+immunosorbent graphite powder. Green represents the activated Screen Printed Carbon+Porous membrane. Blue represents the activated Screen Printed Carbon.

The voltammetric response and redox cycling of the reversible Ferricyanide-ferrocyanide couple is commonly used as an educational tool to introduce electrochemistry. Potassium Ferricyanide in 50 mL of 1 M potassium nitrate to final concentrations of 1 and 2 mM was used. The Ferricyanide redox response forms the characteristic "duck" shape of a fully reversible reaction in the cyclic voltammogram, shown in FIG. 3.

Chip Sensor Fabrication

The present invention is a carbon screen print electrode disposable element chip from different sources in the U.S. Further development of the chip is needed in order to use it in detection of pathogens such as bacteria, parasites, toxins, and viruses. The immobilized antibody or antigen on the carbon immunosorbent (also called modified carbon paste) is deposited on the top of the working electrode only. A layer of hydrophilic membrane with a pore size smaller than the carbon particles is used to retain the modified carbon paste and prevent electrical shorting of the electrodes or signal generation at the reference and counter electrodes. This layer also prevents any loose carbon from being flushed out.

A pathway for defining the flow from an inlet to an outlet and to join an acrylic manifold to carry different solutions to the carbon screen print electrode has been constructed. The fluidic pathway is defined by a laser or a knife cutting the pattern into the membrane.

Silicone tubing was used for the inlet of the chip which is attached to a measuring device as described in U.S. Pat. No. 7,931,788, or 8,652,311, or a use of new wireless phone technology to detect the signal. All other tubing used for all the fluids were silicone tubing. The flow rate was calibrated for different values. A flow rate range of between 0 to 6.5 uL/sec were tested and 3.0 uL/sec was used for the testing.

FEP (fluorinated ethylene propylene) tubing 1 mm. times 0.5 mm was also used for the sensor inlet and outlet ports.

Rabbit IgG, anti rabbit-IgG antibodies, peroxidase labeled Goat anti-IgG (conjugate), peroxidase labeled Goat anti-*peromyscus leucopus* IgG, phosphatase labeled Goat anti-*peromyscus leucopus* IgG were obtained from Sigma Chemical Co. (MO, USA) for testing. Sodium phosphates (Monobasic), sodium phosphate (Dibasic), sodium acetate (Trihydrate), Sulphuric Acid were obtained from Fisher Scientific Co. (NJ, USA) for testing. Sodium chloride, sodium hydroxides were obtained from JT Baker (NJ, USA) for testing. Tween 20 (Polyxyethylenesorbitan Monolaurate) was obtained (NJ, USA) for testing. Tween 20 (Polyxyethylenesorbitan Monolaurate) was obtained from Sigma Chemical Co. (MO, USA) for testing. ULTI (Ultra Low Temperature Isotropic carbon) was obtained from Carbon Medics Inc. (TX, USA). Woodward's reagent K (N-ethyl-5-phenylisoxazolium-3'-sulfonate), Trypsin inhibitor, Bovine Serum Albumin, Hydrogen Peroxide (30% v/v aqueous solution), α-Naphthyl phosphate were obtained from Sigma Chemical Co. (MO, USA). Hydrochloric acid, Sodium Hydroxide, Sodium Iodide was obtained from JT Baker (NJ, USA) for testing.

Preparation of Modified Carbon or Graphite Powder Immunosorbent

Woodward's reagent K immobilization is a technique for obtaining covalent linkage of the proteins to the surface of the carbon (covalently linked immuno-reagent-solid phase conjugates). First, an activation of the solid support is performed. Second, coupling of the antibody to the activated solid support occurs. It does not leave traces of itself after the process.

The pH of the solution with Woodward's reagent K (20 mg/ml) in water was adjusted to 4.5 using diluted NaOH solution, followed by suspension of 25 mg of ULTI carbon (product of Carbon Medics Inc.) in 1 mL of it. This is followed by incubation at room temperature for 2 hours with shaking. The suspension was later washed 5 times with distilled water by repeated centrifugation and removal of the supernatant. Carbon thus treated with Woodward's reagent K was suspended in 1 mL of a solution of IgG (0.5 mg/mL). The suspension was incubated at room temperature for 2 hours with shaking. After incubation, the carbon particles are again washed five times with distilled water with repeated centrifugation and removal of the supernatant. 5 mg of trypsin inhibitor is then added to the same suspension as a blocking agent and incubated for an additional 2 hours at room temperature with shaking. The suspension was finally washed 5 times with PBS by repeated centrifugation (5 minutes each) and removal of the supernatant. The immunosorbent was stored in the same buffer solution at four degrees Celsius.

Preparation of Graphite Powder onto Screen Printed Carbon

Screen print electrodes (carbon working, carbon counter, silver or any other reference electrode) were activated by submerging in 0.1 M Na-phosphate buffer and running a Chrono Ampere (CA) at +1.3 V for 3 minutes. The immunosorbent was mixed thoroughly to ensure graphite powder suspension.

The screen print electrode was covered with the porous hydrophilic membrane and then a layer of the membrane over the entire strip (the WE, CE, and RE). Immunosorbent 10-15 ul was used to cover the screen print working electrode. The electrodes were place at 37 degrees Celsius for 5-7 minutes to dry, and then electrodes were packaged with fluidic channels for the experiment.

The Measuring System

The measuring system or measuring circuit used is the one which was described in U.S. Pat. No. 7,931,788 without the sensing element part. Therefore, the chip is attached to the measuring device in order to get a signal. Any wireless technology can be used to transfer and record the signal. Newly developed wireless phone devices can also be used to receive a test signal.

Highly dispersed carbon or carbon paper or any conductive powder that can offer a large surface area to volume ratio, and at the same time placed on the top of the working electrode, can function as a working electrode because of its conductive nature or it can work as an electrode itself or without being the electrode. The material possesses characteristic area per unit mass and the particle size form lies in the same order of magnitude as that of proteins. This provides the basis for immobilization of antibodies on this carbon. Such a process enhances the proximity of biological components with the transducer, a very essential factor for biosensor development. ULTI is used as a material for the immunosorbent in a finely dispersed powder form (a fraction less than 275 mesh size of an ASTM sieve). Current collection is achieved through the working carbon electrode, while another carbon represents the counter electrode, and silver as the reference electrode respectively. Amperometry is a technique where the output of the sensor is current, which is measured by applying a constant potential between the working and reference electrodes. The signal is due to the electrochemical process involving the analyte, taking place at the electrode surface. The potential difference is termed working potential and is determined by cyclic Voltammetry.

The ULTI, graphite, carbon immunosorbent is modified by immobilized IgG or any antibody antigen immuno chemical. This is a "sandwich immunoassay" technique for detection of the carbon, containing immobilized antibodies. The immobilized carbon was added on the center of the printed screen sensor of the disposable sensing element (the working electrode). The small size of carbon particles increases the rate of immuno-interaction at each stage. Horseradish peroxidase (HRP) or alkaline phosphatase (AP) attached as a label to the anti-human IgG catalyses the oxidation of iodide into iodine. Electrochemical reduction of iodine forms the basis for determination of the activity of HRP or AP enzyme and quantification of the enzyme label. The scheme of reaction is as follows:

$$2I^- + H_2O_2 + 2H^+ \rightarrow I_2 + 2H_2O_2 \quad \text{(Equation 0.1)}$$

$$I_2 + 2e^- \rightarrow 2I^- \quad \text{(Equation 0.2)}$$

The amount of iodine formed by reaction Equation 1, detected using reaction Equation 2, is a measure of the activity of HRP or AP label. Since the amount of antigen (analyte) determines the amount of HRP-labeled antibodies that bind to form the sandwich, amperometric measurement of iodine formed is directly proportional to the analyte concentration. The sandwich complex replaced by alkaline phosphatase labeled immuno-conjugate (AP) where HRP was previously used, where the hydrolysis of .alpha.-Naphthyl Phosphate to .alpha.-Naphthol is determined amperometrically.

$$\alpha\text{-Naphthyl Phosphate} + H_2O\text{-AP} \rightarrow \alpha\text{-Naphthol} + HPO_4^{-2} \quad \text{(Equation 0.3)}$$

Results

The assay procedure described above was used initially to test the response of the system using rabbit IgG as the analyte. The rabbit IgG is immobilized on the immunosorbent and anti-rabbit IgG is used as antibody. Anti-rabbit IgG is labeled and alkaline phosphatase labeled anti-rabbit were used separately.

The data for both the type of the conjugates indicate the data is good. But the alkaline phosphatase labeled conjugate gave higher current than Horse Radish peroxidase labeled conjugate. This implies that the reaction of α-Naphthyl Phosphate to α-Naphthol yields higher current than the reduction of iodine to iodide. Hence, further experiments were done using alkaline phosphatase labeled conjugate.

A Control experiment of cyclic Voltammetry (CV) was performed using Ferricyanide and the screen print electrode disposable sensing element in monitoring redox (reduction-oxidation) of Ferricyanide using cyclic Voltammetry. Ferricyanide is a common oxidant in organic chemistry and has been used as a probe for a variety of organic and biological reactions, as the reduction of Ferricyanide to ferrocyanide is easily monitored. The screen print electrode disposable sensing element performance is described in FIG. 3, which illustrates the results.

Blue indicates the activated screen printed carbon,

Green is the activated screen printed carbon+porous membrane,

Red is the activated screen printed carbon+porous membrane+immobilized immuno-absorbed on graphite powder.

Another testing of the disposable sensing element with the device in U.S. Pat. Nos. 7,931,788 and 8,652,311 to get the signal or any other wireless technology can be used to transfer and record the signal. A newly developed wireless phone device can also be used to receive a test signal. Duplicate testing yielded good and similar results. The read-out from the device for a 10 ug/mL sample and using IgG (Phosphate buffer saline Tween) PBST sample was as follows:

The buffer (buffer solution back ground current)=3.1 (micro Ampere) . . . µA.

The SS (Steady State current)=8.1 (micro A) µA

Therefore the Diff (Difference)=5.0 (micro A) µA

CONCLUSION

The potential of the portable amperometric carbon screen print electrode will be demonstrated based on total *E. Coli, L. monocytogenes*, and *campylobacter C. Jejuni* as antigen and highly dispersed flow immunoelectrode for fast determination of the above infection in blood serum, drinks, food, saliva, or urine under field conditions. The system design is based on an amperometric carbon screen print electrode that employs disposable sensing elements. This approach combines the advantages of utilization of highly dispersed immunosorbent, flow over scheme of immunoassay, and highly sensitive electrochemical determination of enzyme labels. A main benefit of total *E. Coli*, of *L. monocytogenes*, and *campylobacter C. Jejuni* concentration or recombinant nucleocapsid antigen application in immunoassay is that antigen preparation is easy to standardize. Since the principle of disposable sensing elements is involved, there has been no regeneration of immunosorbent between measurements.

The format of the assay and its proven applicability make it suitable for standardized use at fields located at remote sites, with minimal technical expertise. The carbon screen print electrode can be used to discrete the samples (positive and negative) without any pretreatment of the samples in a well-defined time interval (25 minutes). The device is extremely useful for studies relating to population screening of Hantavirus in mice or human blood in remote areas with limited facilities, to simplify blood collection and reduce costs without unduly sacrificing analytical accuracy. The device can be easily adapted for fast analysis of other microorganisms in biological, physiological and analytical practices under non-laboratory conditions and field operations such as bacteria, toxins, and parasites.

What is claimed is:

1. A biosensor comprising:
    a flat plate;
    a carbon working electrode
    a carbon counter electrode, and
    a silver reference electrode
    all attached to said flat plate;
    said electrodes are in spaced apart relation and are screen-printed electrodes, and connected to a respective conductive lead and a measuring circuit;
    a hydrophilic membrane attached to said electrodes;
    a polymethacrylate
    transparent thermoplastic layer having two surfaces, including on both surfaces a clear, thin flexible plastic film;
    a carbon or graphite powder including a chemically bonded antigen or antibody immunosorbent deposited on said working electrode;
    a fluidic chamber containing said screen-printed electrodes, hydrophilic membrane, coated polymethylacrylate layer and said carbon or graphite powder,
    a first inlet PTFE tube adhered in said glue for selective connection to at least one analyte fluid and a second outlet PTFE tube for discharge of said fluid after processing; wherein when a fluid is introduced through said inlet, it flows through a vertical hydrophilic membrane, then flows horizontally over said immunosorbent with said antigen or antibody creating a reaction so that said fluid interconnects said working electrode and said reference electrode producing a current signal through said leads and said measuring circuit, and the fluid finally is discharged through said outlet.

2. The biosensor of claim 1 wherein said inlet tube is selectively connectable to multiple fluid sources in a sequence of operations.

3. A biosensor comprising:
    an elongated bottom disposable layer comprising:
        a flat plate;
        a working electrode, a counter electrode, and a reference electrode all attached to said flat plate;
        said electrodes in spaced apart relation, each connected to a respective conductive lead and a measuring circuit;
        an immunosorbent layer overlying said working electrode comprising
        a conductive with a chemically bonded antigen or antibody;
        a vertical hydrophilic pore membrane layer attached to said immunosorbent layer and overlying at least said working electrode;
        a fluid impermeable layer overlying said vertical pore membrane layer,
        said fluid impermeable layer having an arcuate opening that substantially overlies the three electrodes so as to define
            a microfluidics chamber;
        a cover layer overlying said fluid impermeable layer so as to define
            an enclosed microfluidics chamber that includes said electrodes, said cover layer including an inlet at one end of said arcuate opening and an outlet at the opposite end; wherein when a fluid is introduced through said inlet it flows through said vertical pore membrane, then flows horizontally over said immunosorbent carbon with said antigen or antibody creating a reaction so that said fluid becomes conductive so as to interconnect said working electrode, said counter-electrode and said reference electrode producing a current signal through said leads and said measuring circuit, and the fluid flows through said outlet.

4. The biosensor of claim 3 wherein said reference electrode is silver.

5. The biosensor of claim 3 additionally comprising a transmitter for transferring the current signal to a remote location via a special connection.

6. The biosensor of claim 3 wherein said analyte does not require pre-enrichment.

7. The biosensor of claim 3 wherein the microfluidics chamber allows the analyte to flow over the immunosorbent layer.

8. The biosensor of claim 3 additionally is part of a portable rapid handheld device containing the biosensor and the measuring circuit and additionally comprising a readout for displaying the status of the current signal.

9. The biosensor of claim 8 wherein the device is small enough to be held in one hand.

10. The biosensor of claim 8 wherein said device includes a transmitter for wireless communication with a readout.

11. The biosensor of claim 8 wherein said device includes a microprocessor control so it can be automated for controlling through multiple channels a selected sequence of analytes and washes to determine the presence of any microbes.

12. The biosensor according to claim 3, wherein the conductive material in the immunosorbent is selected from a group consisting of carbon, graphite, and ULTI immunosorbent.

13. The biosensor according to claim 12, wherein the conductive immunosorbent is made of conductive carbon powder particles.

14. The biosensor according to claim 13 wherein the biosensor has a special pore membrane layer in which there are vertical pores of a size smaller than the powder particles.

* * * * *